(12) United States Patent
Aiat

(10) Patent No.: US 12,064,066 B2
(45) Date of Patent: Aug. 20, 2024

(54) DISPLAY DEVICE, LIQUID DISPENSER, AND USE OF A DISPLAY DEVICE ON A LIQUID DISPENSER

(71) Applicant: Anas Aiat, Freiburg (DE)

(72) Inventor: Anas Aiat, Freiburg (DE)

(*) Notice: Subject to any disclaimer, the term of this patent is extended or adjusted under 35 U.S.C. 154(b) by 337 days.

(21) Appl. No.: 17/441,751

(22) PCT Filed: Mar. 19, 2020

(86) PCT No.: PCT/EP2020/057648
§ 371 (c)(1),
(2) Date: Sep. 22, 2021

(87) PCT Pub. No.: WO2020/193371
PCT Pub. Date: Oct. 1, 2020

(65) Prior Publication Data
US 2022/0175196 A1    Jun. 9, 2022

(30) Foreign Application Priority Data
Mar. 22, 2019    (DE) .......................... 102019107418.5

(51) Int. Cl.
*A47K 5/12* (2006.01)
*A61L 2/00* (2006.01)
*G09F 9/33* (2006.01)

(52) U.S. Cl.
CPC .......... *A47K 5/1217* (2013.01); *A61L 2/0088* (2013.01); *G09F 9/33* (2013.01); *A47K 2005/1218* (2013.01); *A61L 2202/14* (2013.01); *A61L 2202/15* (2013.01)

(58) Field of Classification Search
CPC .......... A47K 5/1217; A47K 2005/1218; A61L 2/0088; A61L 2202/14; A61L 2202/15; A61L 2202/17; G09F 9/33; G08B 21/245; G01F 11/00
See application file for complete search history.

(56) References Cited

U.S. PATENT DOCUMENTS

| | | | |
|---|---|---|---|
| 5,695,091 A * | 12/1997 | Winings | A47K 5/1217 222/39 |
| 2005/0133100 A1* | 6/2005 | Bolderheij | E03C 1/0404 137/801 |
| 2009/0077736 A1* | 3/2009 | Loberger | E03C 1/057 4/619 |
| 2015/0223646 A1 | 8/2015 | Weggelin et al. | |
| 2017/0215655 A1* | 8/2017 | Ophardt | G06F 3/167 |

FOREIGN PATENT DOCUMENTS

| | | |
|---|---|---|
| DE | 102015100201 | 7/2016 |
| DE | 102018203616 | 9/2019 |
| EP | 3336817 | 10/2019 |
| WO | 2009094790 | 8/2009 |
| WO | 2016041583 | 3/2016 |
| WO | 2017186688 | 11/2017 |

* cited by examiner

*Primary Examiner* — Donnell A Long
(74) *Attorney, Agent, or Firm* — Volpe Koenig

(57) ABSTRACT

A display device (3) on a liquid dispenser (1), the display device having at least one display element (4) and a drive device (5) for moving the display element (4) between an initial position and a display position. The drive device (5) is provided with an interface (6), via which the drive device (5) can be connected to a dispensing device (2) of the liquid dispenser (1) such that the drive device (5) is automatically activated by the actuation of the dispensing device (2) of the liquid dispenser (1).

19 Claims, 4 Drawing Sheets

US 12,064,066 B2

DISPLAY DEVICE, LIQUID DISPENSER, AND USE OF A DISPLAY DEVICE ON A LIQUID DISPENSER

INCORPORATION BY REFERENCE

The following documents are incorporated herein by reference as if fully set forth: PCT Patent Application No. PCT/EP2020/057648, filed Mar. 19, 2020, and German Patent Application No. 10 2019 107 418.5, filed Mar. 22, 2019.

TECHNICAL FIELD

The invention relates to display devices that are configured for use on and/or with a liquid dispenser, to a liquid dispenser and to the use of a display device on a liquid dispenser.

BACKGROUND

Liquid dispensers are used, for example, as cleaning agent dispensers or soap dispensers for hand cleaning, and as disinfectant dispensers for hand disinfection.

Studies show that proper hand cleaning and hand disinfection are very useful ways of effectively avoiding the spread of infectious diseases. In medical facilities, for example doctors' practices and hospitals, the risk of infection and of the spread of infectious diseases is particularly high. Proper hand disinfection is thus in this case particularly important and effective for stopping the spread of infectious diseases and protecting oneself as well as the persons present there against infection.

In medical facilities such as doctors' practices and hospitals, it is known to establish so-called disinfection plans. The disinfection plans contain information and instructions relating to how often, on what occasions, and in particular how proper hand disinfection is to be carried out. This is because it has been found that the protective effect that can be achieved with hand disinfection depends crucially on carrying out the hand disinfection regularly, at the appropriate time and in the appropriate way. Accurately following the rules and guidelines relating to hand disinfection is therefore important in order to be able to prevent a spread of infectious diseases, especially in the aforementioned medical facilities.

By regular training and notices, attempts are made to indicate the need to follow the rules provided for proper hand disinfection in order to effectively avoid the spread of infectious diseases, and thus improve so-called compliance in connection with proper hand disinfection.

Such measures have the effect for a certain time that the rules for proper hand disinfection are followed better. It may also be found, however, that the positive effect of these measures decreases even after a short time and the rules for hand disinfection are then followed more laxly. This has the consequence that hand disinfection is no longer carried out often enough, no longer at the appropriate times and no longer in the prescribed way. This is referred to as noncompliance with the guidelines for hand disinfection. One reason for this noncompliance may be the way in which the required hand disinfection is indicated. Often, message boards and notices that contain instructions relating to proper hand cleaning and hand disinfection are used. The older these message boards and notices are, the less they are observed and obeyed. One reason for this is habituation or adaptation to the message boards and notices. Ultimately, this leads to increasing noncompliance with the guidelines for hand disinfection, with the result that the transmission risk of infectious diseases increases again, especially in hospitals and doctors' practices.

SUMMARY

It is therefore an object of the invention to provide a display device, a liquid dispenser and a use of a display device, which can promote accurate following of rules for proper hand disinfection.

This object is firstly achieved by a display device having one or more of the features disclosed herein that relate to such a display device. In particular, in order to achieve the object, a display device that is configured for use on and/or with a liquid dispenser is therefore proposed, which has at least one display element and a drive device for moving the at least one display element between an initial position, in particular concealed from a user of the liquid dispenser, and a display position. In this case, the drive device has an interface, by means of which the drive device can be connected, and is connected in the position of use, to a delivery device of a liquid dispenser in such a way that the drive device can be activated by actuating the delivery device of the liquid dispenser.

In this way, it is possible for the drive device of the display device to be activated automatically by actuating the delivery device of the liquid dispenser, so that the at least one display element travels from its preferably concealed initial position into its visible display position. If the display element carries positive information, for example text and/or a symbol, for example a smiley, the user of the liquid dispenser receives positive feedback as a consequence of using the liquid dispenser. The positive feedback imparts a positive feeling to the user. By the positive feeling, the user is encouraged to use the liquid dispenser more often. This may have the effect that, for example, hand disinfection is carried out more often because of the positive feedback that the display device provides when the liquid dispenser is used. The feedback carried out by the display device may achieve a positive educational effect, contribute to explanation, for example in relation to the topic of hand hygiene, and furthermore condition the users to the need for hand cleaning and hand disinfection. Overall, this may promote the following of predetermined disinfection plans for hand disinfection and/or hand cleaning plans. By means of the display element, it is naturally also possible to provide warnings, prompts, instructions and/or information in connection with hand disinfection and/or hand cleaning.

At this point, it should be mentioned that the at least one display element may be a support of various information and/or feedback. Depending on the target group, it is also possible for example to deliver technical information, which relates to topics such as infectious diseases and hand disinfection, by means of the at least one display element. It is in this case simplest for the display element to have or be a printed or written sign or a printed or written card. Thus, besides positively presented images, it is also possible to provide positive information texts, messages, and/or statistics in relation to hand disinfection, by means of the display element. It is, however, also possible to equip the at least one display element with a two- or three-dimensional design and/or figure, in order to attract the user's attention and/or provide feedback after use of the liquid dispenser.

Particularly if the display element is arranged concealed, for example concealed in a housing of the display device, and therefore not visible to the user, in its initial position, the positive unexpected effect of the display device may be sustained for a longer time. Visual fatigue of the information displayed by means of the display element, such as for example often occurs in the case of a constantly visible notice, may thus be avoided, or at least delayed. The display device furthermore allows feedback that takes place in direct response to the use of the liquid dispenser and is therefore perceived by the user as more personal than is the case, for example, with notices. By the direct feedback and addressing, the attention of the users may be increased and the compliance with the hygiene provisions may be improved.

In a further embodiment, a display device that is configured for use on and/or with a liquid dispenser is therefore proposed, wherein the display device has at least one sensor, for example a presence sensor, and wherein the display device can be activated in order to emit a signal and/or information by triggering the at least one sensor. As soon as the presence of a person in the vicinity of the display device, and therefore also in the vicinity of a liquid dispenser equipped with such a display device, is detected with the aid of the sensor, configured for example as a presence sensor, which may for example also be a motion sensor, the display device is activated automatically and a signal and/or information is emitted. The signal and/or the information may make the person aware of the liquid dispenser and optionally even request them to carry out hand disinfection. For example, a positive message and/or communication may be used as information.

In one embodiment of the display device, a combination of multiple features as disclosed herein relating to a display device is provided. In this way, a display device which is configured for use on and/or with a liquid dispenser and which has at least one display device, a drive device for moving the at least one display element between its initial position and its display position, and a sensor, in particular a presence sensor, is provided. If the sensor of the display device is configured as a presence sensor, the display device is configured to detect a person in the vicinity of the display device. As soon as the presence sensor is triggered by the presence of a person, the display device may be activated automatically. This may mean that the drive device of the display device is activated. By activating the display device, the at least one display element is moved from its initial position into its display position and a person in the vicinity of the liquid dispenser is made aware of the liquid dispenser.

In this context, it may be advantageous for the interface of the drive device to be configured to receive and/or process a sensor signal of at least one sensor, for example of the aforementioned presence sensor and/or of another sensor, in particular of a switch and/or a button. The drive device may thus be activated automatically when the sensor is triggered. In this context, it may be advantageous for the drive device to have a sensor signal input, by means of which activation of the drive device may be carried out.

By means of the sensor signal input, the display device may for example be connected to at least one sensor of the display device, which simultaneously functions as an opening sensor of an automatic door. If the opening sensor of the door is triggered, on the one hand the door is opened. On the other hand, a corresponding activation signal may be transmitted to the sensor signal input of the display device and the display device, in particular its drive device, may be activated.

The door may in the simplest case be assigned a button and/or switch of the display device as a sensor, which is connected to a sensor signal input, for example the sensor signal input already mentioned above. If the door is opened manually or automatically, the sensor, button and/or switch may be triggered and the display device may correspondingly be activated.

As already mentioned above, the display device may therefore have, for example, a presence sensor and/or a motion sensor and/or a button and/or a switch as at least one sensor.

In one embodiment of the display device, it has an optical signal transducer, in particular a lamp, particularly preferably an LED lamp. The optical signal transducer may, for example, be activated when the presence of a person has been detected with the aid of the presence detector already mentioned above. It is, however, also possible to activate the optical signal transducer when the delivery device of the liquid dispenser is actuated. For this purpose, it may be expedient for the optical signal transducer to be connected to the interface of the drive device of the display device. The interface may for this purpose have an electrical switch and/or a button which, when the delivery device of the liquid dispenser is used, is automatically actuated and activates the optical signal transducer.

It is furthermore possible for you display device to have an acoustic signal transducer. By means of the acoustic signal transducer, it is possible to emit an acoustic signal, for example a sound or a sound sequence, in order to draw attention to the liquid dispenser which is connected to the display device, and/or to provide feedback relating to the use of the liquid dispenser. The activation of the acoustic signal transducer may, for example, be carried out by means of the presence sensor already mentioned above. If the presence of a person in the vicinity of the display device is detected, the acoustic signal transducer is activated and a sound or a sound sequence is emitted. The acoustic signal transducer may also be activated by actuating the delivery device of the liquid dispenser and/or by activating the drive device of the display device. During and/or after actuation of the delivery device of the liquid dispenser, which is equipped with the display device, it is thus possible to emit by means of the acoustic signal transducer an acoustic signal that is presented as positively as possible and/or is as pleasant as possible. In this context, it may be advantageous for the interface to have an electrical switch and/or a button which, when the delivery device of the liquid dispenser is used, is automatically actuated and activates the acoustic signal transducer.

In one embodiment of the display device, the drive device and/or an acoustic signal transducer, for example the acoustic signal transducer already mentioned above, and/or an optical signal transducer, for example the optical signal transducer already mentioned above, of the display device may be activated by triggering a sensor, for example the sensor already mentioned above, in particular the presence sensor, of the display device.

In one embodiment of the display device, which is particularly simple in terms of design, the drive device has a linkage. The linkage may be arranged between the interface of the drive device and the at least one display element. With the aid of the linkage, an actuation movement which is exerted on the delivery device of the liquid dispenser, which with the display device, may be converted into the movement of the at least one display element from its initial position into its display position. The linkage may for example be a gear linkage, a mechanical linkage and/or a pinion linkage. The pinion linkage may have at least one rack. The drive device may also comprise a control wire in order to because the at least one display element between the initial position and the display position.

The drive device may comprise a freewheel mechanism. The freewheel mechanism may be configured to decouple an actuation element connected to the drive device, for example an actuation lever, of a liquid dispenser from the display element when the actuation element is moved back into its initial position after actuation. The display element may thus remain in its display position even when the actuation element of the delivery device of a liquid dispenser equipped with the display device is returned back into its initial position.

The linkage, particularly if it is a gear linkage, for example a pinion linkage, may be provided with a freewheel mechanism, for example the freewheel mechanism already mentioned above, which prevents a restoring movement of an actuation element, connected to the linkage by means of the interface, into its unactuated initial position from leading to a forced restoring movement of the display element into its initial position. A liquid dispenser equipped with the display device may thus be activated repeatedly without the display element being retracted from the display position into its initial position in between.

In order to be able to connect the drive device of the display device to a delivery device of a liquid dispenser, it may be advantageous for the interface to have a coupling. By means of the coupling of the interface, the drive device, in particular a linkage of the drive device, may be connected, preferably mechanically, to a delivery device of a liquid dispenser. An actuation movement of the delivery device may thus be transmitted automatically to the drive device of the display device by means of the coupling of the interface. The coupling may be releasable in order to stop transmission of an actuation movement of the delivery device to the drive device if required. The coupling may for example be a friction coupling which, beyond a defined resistance force, allows further movement of an actuation element of the delivery device of a liquid dispenser without continuing to transmit this movement to the drive device. The drive device may thus for example have a movement limiter, for example a limiting stop, which prevents further movement of the display element beyond its display position. Once the display element has reached the display position, the releasable coupling, in particular the friction coupling, allows further movement of the actuation element even though the display element has already reached its display position.

The coupling may also comprise a freewheel mechanism. With the freewheel mechanism, it is possible to prevent a restoring movement of an actuation element, connected to the drive device by means of the interface and the coupling, into its unactuated initial position from leading to a forced restoring movement of the display element into its initial position. A liquid dispenser equipped with the display device may thus be actuated repeatedly without the display element being retracted from the display position into its initial position in between.

In one embodiment of the display device, the drive device has an actuator, in particular an electrical actuator, with which the at least one display element can be moved from its initial position into its display position. The actuator may for this purpose be connected to the aforementioned interface of the drive device. By means of the interface, the actuator may receive a corresponding activation signal, by which it is activated. The activation signal may be a sensor signal of the presence sensor already mentioned above. It is, however, also possible to use an actuation of the delivery device of the liquid dispenser equipped with the display device as an activation signal. In this context, it may be advantageous for the interface of the drive device of the display device to have a switch and/or button, which is switched by actuation of the delivery mechanism of the liquid dispenser and with which the aforementioned actuator can be activated, preferably automatically.

A pneumatic actuator and/or a hydraulic actuator may also be used as an actuator of the drive device. In the simplest case, a pneumatic actuator may comprise at least one air bellows, which can be compressed by actuating the delivery device of the liquid dispenser and by its compression causes an air flow and/or an air displacement by which the display element can be moved at least indirectly between the initial position and the display position. A hydraulic actuator may be constructed in a similar way to the above-described pneumatic actuator.

It is furthermore possible for the interface of the display device to have a sensor signal input for activation of the drive device, in particular of an actuator, for example the aforementioned actuator, of the drive device. The sensor signal input may, for example, be connected to a hand sensor of a liquid dispenser. If the hand sensor is triggered in order to deliver liquid, a signal may be transmitted from the hand sensor to the sensor signal input in order to activate the drive device and the display element may be moved into the display position with the aid of the actuator.

If the display device has a network interface, in particular a wireless network interface, the display device may be activated remotely, for example by a superordinate central unit. It is furthermore possible to transmit information relating to the frequency of use of the liquid dispenser equipped with the display device by means of the network interface to a superordinate central unit. By means of the frequency of use, for example, the suitability of the location of the liquid dispenser may be inferred. If the liquid dispenser is used only rarely, this may mean that its location is poorly selected.

In one preferred embodiment of the display device disclosed herein, at least one display element of the display device is a support, in particular a sign support and/or a figure support. A sign with information, for example in the form of text and/or a symbol, may be applied on this sign support. If required, a sign arranged on the sign support may also be changed, for example in order to avoid or lessen the aforementioned effect of optical fatigue. A two- or three-dimensional figure may also be arranged on a figure support. By alternating information, the users' awareness of a liquid dispenser which is equipped with such a display device may be increased.

The display device may have a delay element, with which a movement of the at least one display element, in particular from its display position back into its initial position, can be delayed. With the aid of the delay element, the display element may be kept in its display position for a certain time after actuation of the delivery device of the liquid dispenser which is equipped with the display device has been carried out. This may reinforce the effect of the display device. The delay element may, for example, be a dampener which is connected to the at least one display element.

In order to achieve the object, a liquid dispenser having a delivery device for delivering liquid, in particular liquid disinfectant, cleaning agent and/or liquid soap, and having a display device having one or more of the features disclosed herein, is also proposed.

The liquid dispenser may, in particular, be a disinfectant dispenser and/or a cleaning agent dispenser and/or a soap dispenser.

In one embodiment of the liquid dispenser, the delivery device is connected to the interface of the drive device of the display device. This ensures that the drive device of the display device is also activated when the delivery device of the liquid dispenser is actuated, so that at least one display element can be moved automatically from its initial position in its display position. In this way, the user of the liquid dispenser receives the desired feedback relating to the use of the liquid dispenser.

Lastly, in order to achieve the object, the use of a display device having one or more of the features disclosed herein, on a liquid dispenser, is also proposed.

BRIEF DESCRIPTION OF THE DRAWINGS

Exemplary embodiments of the invention will be explained in more detail below with the aid of the figures. The invention is not restricted to the exemplary embodiments shown in the figures. Further exemplary embodiments are obtained by combination of the features of individual or several protective claims with one another and/or in combination of individual or several features of the exemplary embodiments. Sometimes in a highly schematized representation:

DETAILED DESCRIPTION

Figure 1:
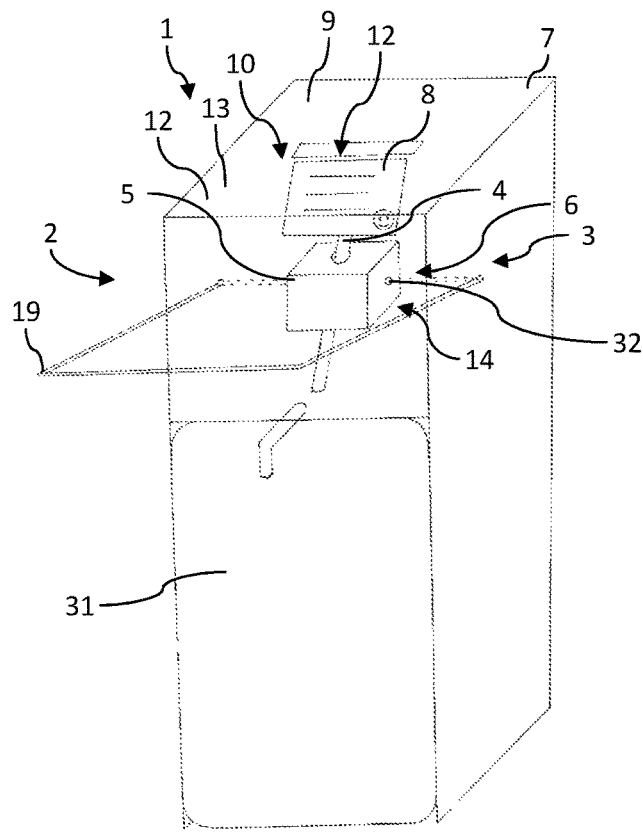
FIG. 1: shows a perspective view of a liquid dispenser having a display device, the display element of which is arranged in an initial position arranged concealed inside the housing of the liquid dispenser.
Figure 2:
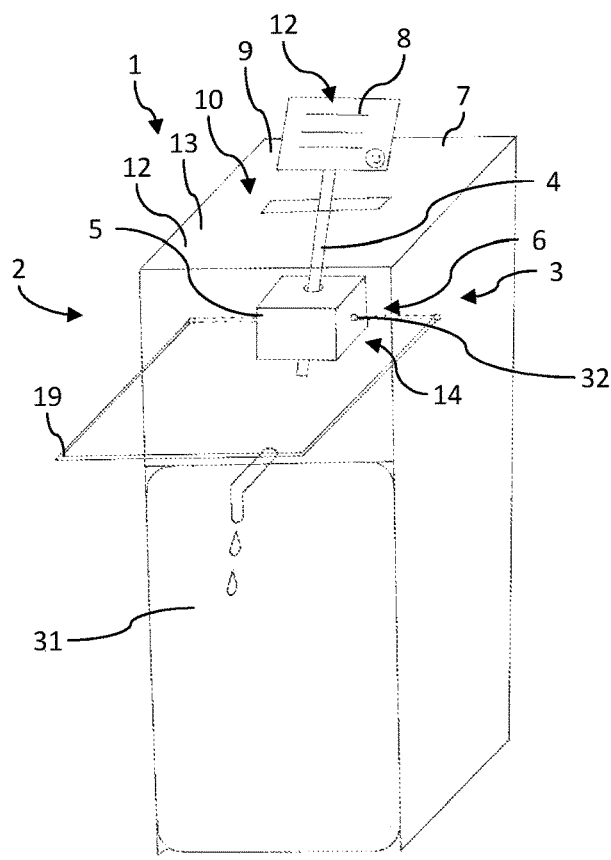
FIG. 2: shows a perspective view of the liquid dispenser represented in FIG. 1, the display element of the display device in this case being arranged in a display position visible to the user of the liquid dispenser.

In the following description of the figures, elements that correspond in their function, even in a different configuration, are provided with corresponding references.

All the figures show at least parts of a liquid dispenser denoted overall by 1, which may for example be used to deliver disinfectant and/or a cleaning agent, for example liquid soap. The liquid dispenser 1 is therefore configured, for example, as a disinfectant dispenser or as a soap dispenser.

The liquid dispenser 1 has a delivery device 2 with which it is possible to deliver liquid, for example liquid disinfectant, liquid cleaning agent and/or liquid soap, for hand cleaning and/or hand disinfection.

The liquid dispensers 1 shown in the figures are furthermore equipped with a display device 3. Each display device 3 has at least one display element 4. The display elements 4 can be moved to and fro by a drive device 5 of the display device 3 between an initial position a display position. The drive device 5 has an interface 6, by means of which the drive device 5 is connected to the delivery device 2, already mentioned above, of the liquid dispenser 1 in such a way that, by actuation of the delivery device 2 of the liquid dispenser 1, the drive device 5 is activated automatically and the display element 4 is moved from its initial position concealed from a user of the liquid dispenser 1 into a visible display position.

The display elements 4 of the different variants of display devices 3 are represented in their display position in FIGS. 2, 3, 6 and 8. In this case, they protrude from a housing 7 of the liquid dispenser 1 so that a sign 8, which is fastened on the respective display element 4, is visible to a user of the liquid dispenser 1 when he or she uses the liquid dispenser 1 by actuating its delivery device 2. Instead of a sign 8, a two-dimensional and/or three-dimensional figure may also be fastened on the display element 4.

The display devices 3 furthermore respectively have a sensor 9 in the form of a presence sensor 9. The respective display device 3 is activated in order to emit a signal and/or information by triggering the presence sensor 9. The activation of the display device 3 by triggering the presence sensor 9 may, for example, consist in moving the display element 4 from its concealed initial position with the aid of the drive device 5 into its visible display position, and in this way making a person detected in the vicinity of the display device 3 aware of the liquid dispenser 1 and requesting them to use it.

Figure 3:
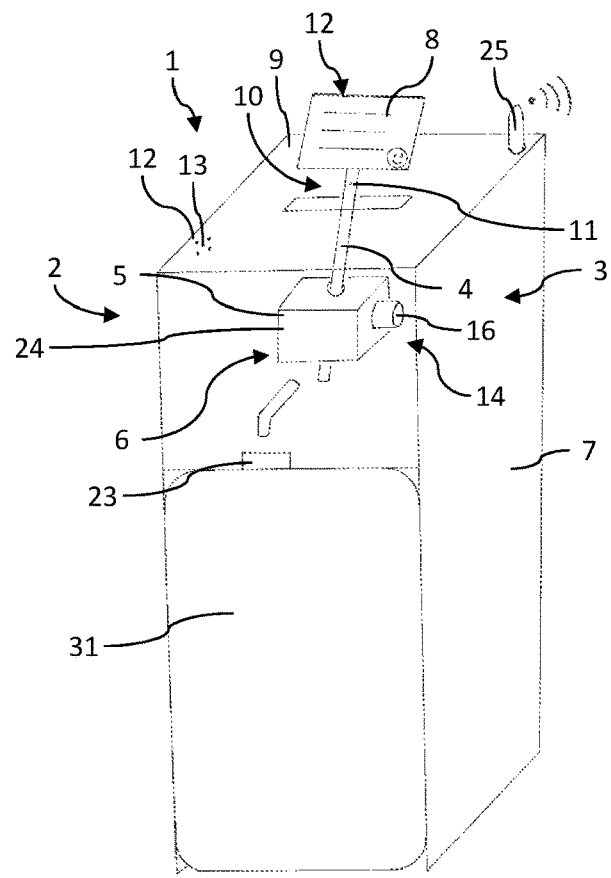
FIG. 3: shows a perspective view of a further liquid dispenser having a display device, a delivery device of the liquid dispenser being actuatable by means of a hand sensor and the liquid dispenser having a wireless network interface with a WLAN antenna.

The aforementioned interface 6 of the drive device 5 of the display device 3 depicted in FIG. 3 is for this purpose configured to receive and process a sensor signal of the presence sensor 9 of the display device 3. All the display elements 4 of the display devices 3 depicted in the figures are configured as sign supports, on the free end of which a sign 8 with a communication or information, preferably positive, is arranged. The display elements 4 have a fastening mechanism 10 for the signs 8, and this can be released with the aid of an actuation element 11 in order to remove the sign 8 from the respective display element 4.

The display elements 4 may also be fitted with signs 8 that are in turn equipped with optical signal transducers 12, for example with LEDs.

The display devices 3 shown in the figures are furthermore equipped respectively with an optical signal transducer 12 in the form of a lamp, for example an LED or a plurality of LEDs, and with an acoustic signal transducer 13. By means of the optical signal transducers 12 and the acoustic signal transducers 13, optical and acoustic feedback relating to the actuation of the respective liquid dispenser 1 can take place. It is furthermore possible to emit corresponding signals by means of the optical signal transducers 12 and the acoustic signal transducers 13 in order to make persons in the vicinity of the display device 3, and of the liquid dispenser 1 equipped therewith, aware of the respective liquid dispenser 1 and request the persons to use it.

By triggering the presence sensor 9, it is possible to activate not only the drive device 5 of the respective display device 3 but also its optical signal transducer 12 and its acoustic signal transducer 13.

The drive devices 5 of the display devices 3 shown in the figures are respectively equipped with a linkage 14. Depending on the embodiment of the drive device 5, the linkages 14 have different transmission elements 15 in order to cause a setting movement of the display element 4 between its initial position and its display position.

In the exemplary embodiment shown in FIG. 3 of a display device 3, it is equipped with an electrical actuator 16. The actuator 16 is connected by means of the linkage 14 and its transmission elements 15 to the display element 4. By actuation of the actuator 16, its movement is transmitted by means of the linkage 14 and the transmission elements 15, for example a pinion 17 which engages with a rack 18, to the display element 4.

Figure 4:
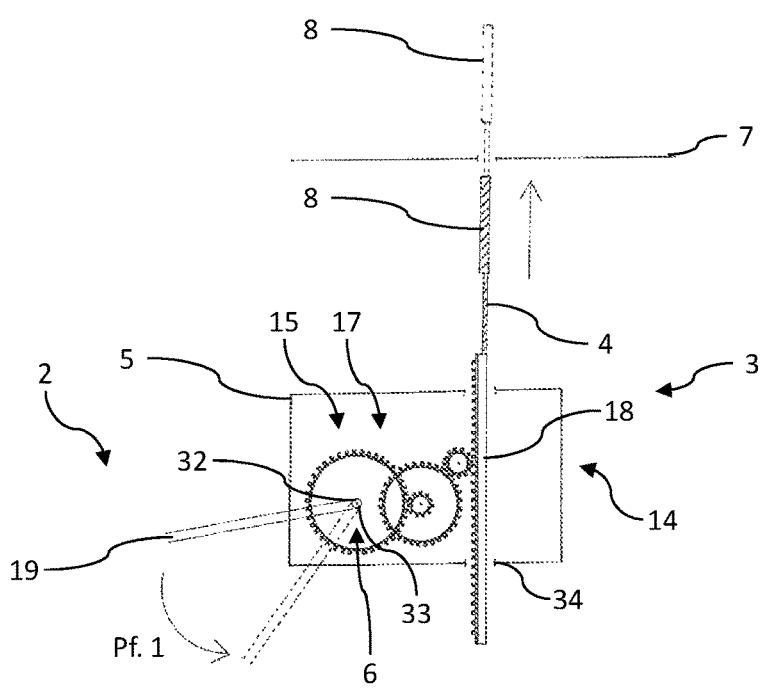
FIG. 4: shows a highly schematized side view of a first embodiment of a drive device of the display device, the drive device comprising a linkage that converts a tilting movement of a lever of the delivery device of the liquid dispenser by means of a plurality of pinions and a rack into a setting movement of the display element of the display device.

The drive device 5 shown in FIG. 4 has a linkage 14 that is configured as a pinion linkage. As transmission elements 15, the pinion linkage has three pinions 17, which engage with one another, and a rack 18 connected to the display element 4. If an actuation element 19, in this case an actuation lever 19, of the delivery device 2 of the liquid dispenser 1 is tilted in the arrow direction in order to deliver liquid from a liquid container 31 connected to the delivery device, this movement is transmitted by means of the interface 6, at which the actuation lever 19 is connected to the first pinion 17 of the linkage 14 of the drive device 5, to the linkage 14 and by means of the linkage 14 ultimately to the display element 4.

Figure 5:
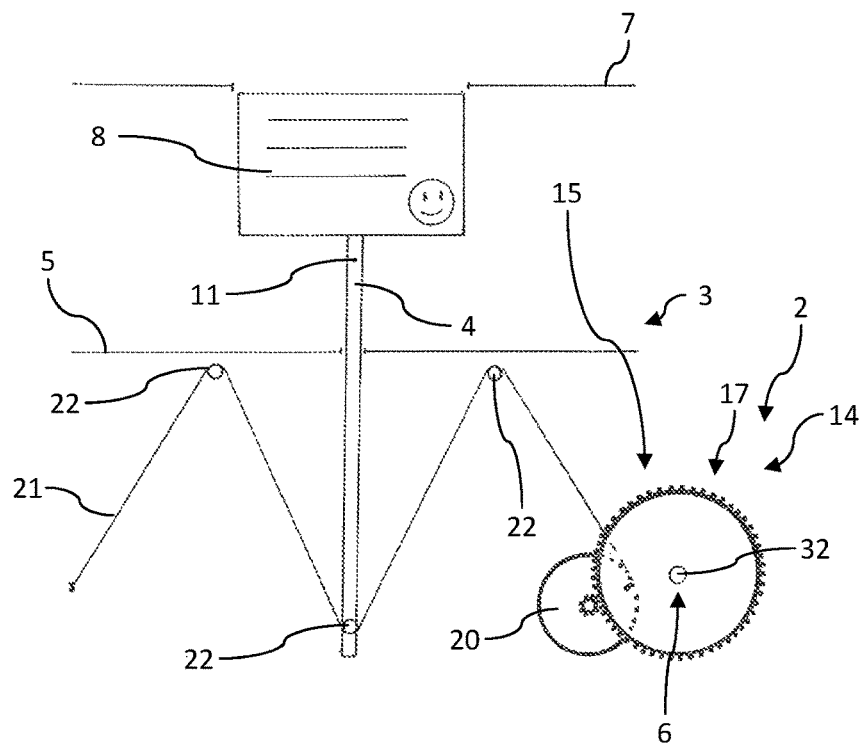
FIG. 5: shows a highly schematized side view of a further embodiment of a drive device of the display device, which comprises a linkage having two pinions, a winding roller, a control wire and three deflecting rollers, the display element provided with a sign display device being represented in its initial position arranged inside the housing of the liquid dispenser.
Figure 6:
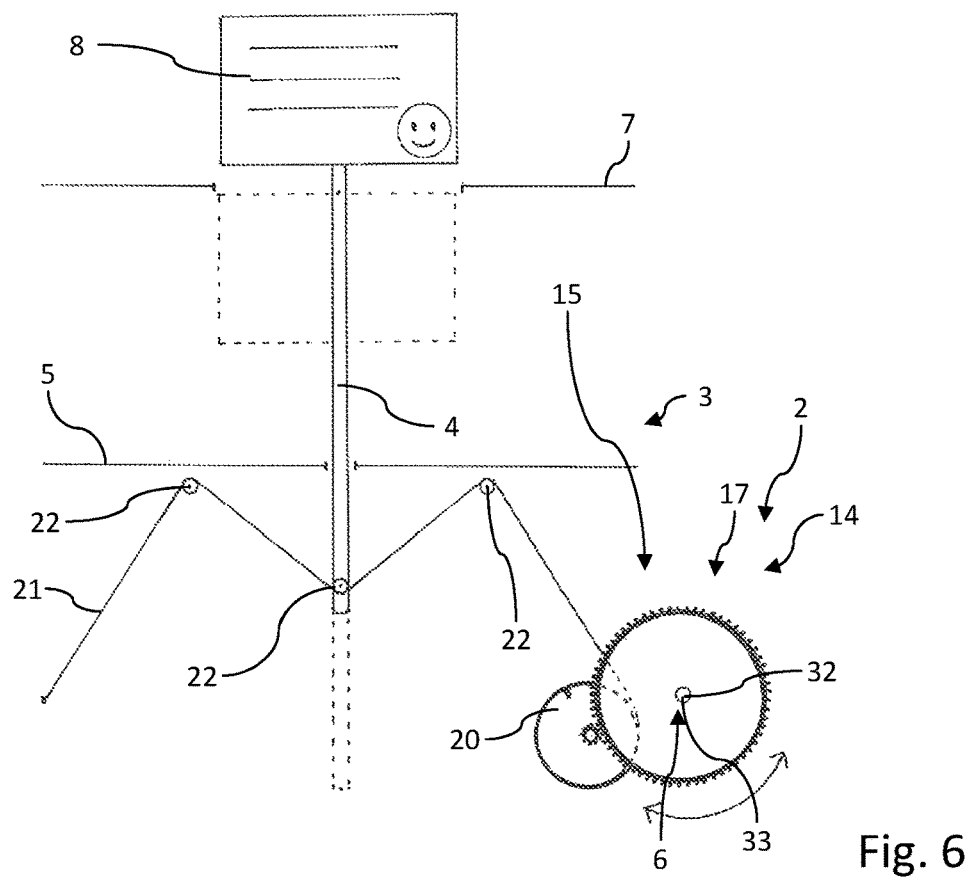
FIG. 6: shows the drive device represented in FIG. 5 with a display element located in the display position.

In the exemplary embodiment shown in FIGS. 5 and 6 of a drive device 5 of a display device 3, the drive device 5 has a linkage 14 that comprises two pinions 17. One of the two pinions 17 is connected to a winding roller 20, onto which a control wire 21 of the linkage 14 can be wound. The control wire 21 runs over three deflecting rollers 22 and is connected to the display element 4. By winding of the control wire 21 onto the winding roller 20, the display element 4 is moved from its initial position shown in FIG. 5, withdrawn in the housing 7 of the liquid dispenser 1, into its display position shown in FIG. 6. The larger of the two pinions 17 has the interface 6 of the drive device 5, by means of which the drive device 5 is connected to the delivery device 2 of the liquid dispenser 1. It is possible to connect the actuation lever 19 shown in FIGS. 1 and 2 to the larger of the two pinions 17 by means of the interface 6, and thus convert a tilting movement of the actuation lever 19 into a winding movement of the winding roller 20.

It is, however, also possible to connect the actuator 16 shown in FIG. 3 to the larger of the two pinions 17 of FIGS. 5 and 6. In this case, an interface 6 of the display device 3 may then be an interface 6 for receiving a sensor signal of a hand sensor 23 which is used for contactless triggering of the delivery device 2 of the liquid dispenser 1 (see FIG. 3).

If a hand is held in the vicinity of the hand sensor 23, the delivery device 2 of the liquid dispenser 1 is activated. At the same time, a sensor signal of the hand sensor 23 may be used to activate the actuator 16, the display element 4 may be moved with the aid of the actuator 16 of the drive device 5 from its initial position into its display position visible to the user. The interface 6 of the drive device 5 may therefore, for example, have a coupling 32 for connection to a delivery device 2 of a liquid dispenser 1. The interface 6 may however also have a switch, a button and/or a sensor signal input 24 for activating the electrical actuator 16 of the drive device 5. The interface 6 of the display device 3 shown in FIG. 3 has a corresponding sensor signal input 24, which receives a sensor signal of the hand sensor 23 and uses it to activate the actuator 16.

The display device 3 represented in FIG. 3 is provided with a wireless network interface 25, which is for example configured to receive and process WLAN signals. In this way, it is possible to carry out remote control of the display device 3 and, for example, to remotely activate the optical signal transducer 12, the acoustic signal transducer 13 and/or also the drive device 5 in order to displace the display element 4.

Each of the display devices 3 shown in the figures may be equipped with a delay element, for example a dampener. With the aid of the delay element, a movement of the display element 4 from its display position back into its initial position may be delayed in order to keep the display element 4, and a sign connected to the display element 4, visible in the display position for a longer time.

Figure 7:
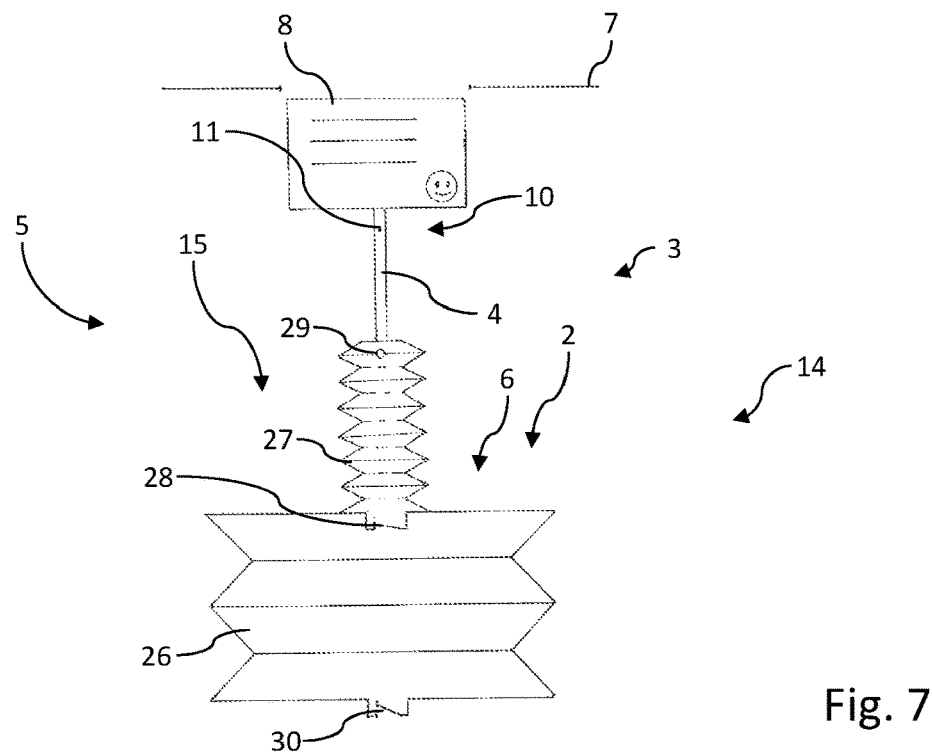
FIG. 7: shows a highly schematized side view of a of a pneumatic drive device of the display device, the pneumatic drive device having an air bellows compressibly in order to displace the display element from its initial position into its display position.
Figure 8:
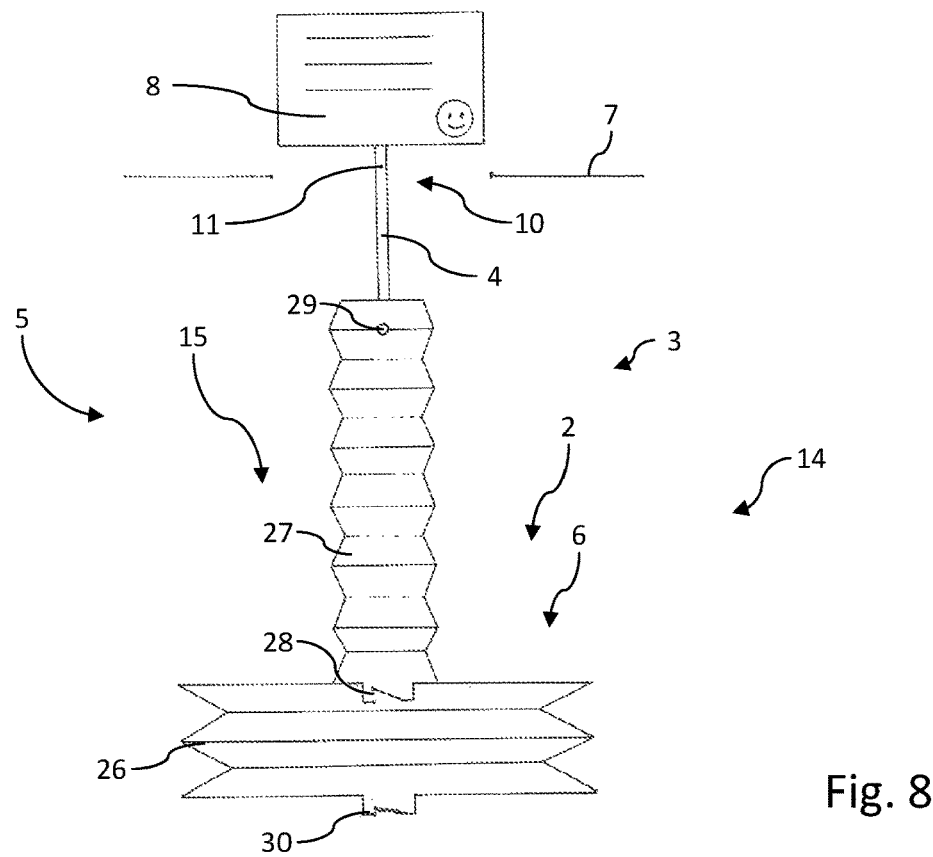
FIG. 8: shows the pneumatic drive device represented in FIG. 7 with a display element located in the display position.

FIGS. 7 and 8 show a further embodiment of a drive device 5 of the display device 3. The drive device 5 is in this case configured as a pneumatic drive device 5. The pneumatic drive device 5 comprises two air bellows 26 and 27, which are connected to one another by means of a nonreturn valve 28 arranged between the lower air bellows 26 and the upper air bellows 27. By compression of the lower air bellows 26, the air contained therein is guided through the nonreturn valve 28 into the upper air bellows 27. The air bellows 27 therefore expands. The air bellows 27 is connected to the display element 4 of the display device 3 and, by its expansion, causes the display element 4 to be moved from its initial position, represented in FIG. 7, inside the housing 7 of the liquid dispenser 1 into its display position according to FIG. 8, in which the sign 8 arranged on the display element 4 protrudes from the housing 7 and is thus visible to a user of the liquid dispenser 1.

Through an outlet opening 29 in the smaller air bellows 27, the air can emerge slowly therefrom. Because of the weight of the display element 4 connected to the air bellows 27 and/or by resilient restoring forces, the air bellows 27 is compressed. Because of the relatively small cross section of the outlet opening 29, the outlet opening 29 functions as a delay element. With the aid of the outlet opening 29, a restoring movement of the display element 4 into its initial position can take place with a delay.

If the air bellows 26 is no longer compressed, it resumes its initial configuration shown in FIG. 7 because of resilient restoring forces. In this case, air enters the air bellows 26 through an inlet valve 30 and refills it for the next actuation.

For the actuation and compression of the larger air bellows 26, the actuation lever 19, already mentioned above, of the delivery device 2 may for example be used. An interface 6 of the drive device 4 is then in the simplest case a bearing surface on which the actuation lever 19 makes contact with the bellows 26 for compression.

The coupling 32 of the drive device 5 shown in FIG. 4 is configured as a friction coupling which, beyond a defined resistance force that acts on the coupling 32 from the side of the drive device 5, allows further movement of the actuation lever 19 of the delivery device 2 of the liquid dispenser 1 without continuing to transmit this movement to the drive device 5. The actuation lever 19 may thus be decoupled from the drive device 5 if required. The coupling 32 is therefore releasable. The drive device 5 has a movement limiter 34, in this case a limiting stop 34, which prevents further movement of the display element 4 beyond its display position. Once the display element 4 has reached the display position, the friction coupling 32 allows further movement of the actuation lever 19 for actuation of the delivery device 2, even though the display element 4 has already reached its display position.

The drive device 5 shown in FIG. 4 is furthermore equipped with a freewheel mechanism 33. The freewheel mechanism 33 allows the actuation lever 19 to be moved back counter to the arrow direction Arr.1 into its initial position, without its movement being converted into a displacement movement of the display element 4. A restoring movement of the actuation lever 19 may therefore be decoupled with the aid of the freewheel mechanism 33 from the drive device 5, and ultimately from the display element 4.

The invention relates to improvements in the technical field of liquid dispensers 1. For this purpose, inter alia, the use of a display device 3, which has at least one display element 4 and a drive device 5 for moving the display element 4 between an initial position and a display position, on a liquid dispenser 1 is proposed. The drive device 5 is provided with at least one interface 6, by means of which the drive device 5 can be connected to a delivery device 2 of the liquid dispenser 1 in such a way that the drive device 5 is activated automatically in order to displace the display element 4 by actuating the delivery device 2 of the liquid dispenser 1.

LIST OF REFERENCES

1 liquid dispenser
2 delivery device
3 display device
4 display element
5 drive device
6 interface
7 housing
8 sign
9 presence sensor
10 fastening mechanism on 4 for 8
11 actuation element of 10
12 optical signal transducer
13 acoustic signal transducer
14 linkage
15 transmission elements
17 pinion
18 rack
19 actuation lever
20 winding roller
21 control wire
22 deflecting roller
23 hand sensor
24 sensor signal input
25 network interface
26 air bellows
27 air bellows
28 nonreturn valve
29 outlet opening
30 inlet valve
31 liquid container
32 coupling
33 freewheel mechanism
34 movement limiter

The invention claimed is:

1. A display device (3) configured for use at least one of on or with a liquid dispenser (1), the display device comprising: at least one display element (4) and having a drive actuator for moving the at least one display element (4) between an initial position and a display position, the drive actuator has an interface (6), by which the drive actuator is configured to be connected to a delivery device (2) of the liquid dispenser (1) such that the drive actuator is automatically activated by actuating the delivery device (2) of the liquid dispenser (1) to move the display element (4) from the initial position, which is concealed from a user of the liquid dispenser (1), into the display position which is visible to a user.

2. The display device (3) as claimed in claim 1, further comprising at least one sensor (9), and the display device (3) is activatable in order to emit at least one of a signal or information by triggering the sensor (9).

3. The display device (3) as claimed in claim 1, wherein the interface (6) of the drive actuator (5) is configured to at least one of receive or process a sensor signal of at least one sensor (9).

4. The display device (3) as claimed in claim 3, wherein the interface (6) has a sensor signal input (24).

5. The display device (3) as claimed in claim 1, further comprising at least one of a presence sensor (9), a motion sensor, a button or a switch as at least one sensor (9), and the display device (3) is activatable in order to emit at least one of a signal or information by triggering the sensor (9).

6. The display device (3) as claimed in claim 1, wherein at least one of the drive actuator, an optical signal transducer (12), or an acoustic signal transducer (13) of the display device (3) is activatable by triggering a sensor (9) of the display device (3).

7. The display device (3) as claimed in claim 1, further comprising a linkage (14) connected to the drive actuator.

8. The display device (3) as claimed in claim 7, wherein the linkage comprises at least one of a gear linkage, a mechanical linkage, a pinion linkage, or a control wire (21).

9. The display device (3) as claimed in claim 7, further comprising a freewheel mechanism (33) connected to the linkage.

10. The display device (3) as claimed in claim 1, wherein the interface (6) has a coupling (32) for connection to a delivery device (2) of the liquid dispenser (1), and the interface (6) has at least one of a switch, button, or a sensor signal input (24) for activation of the drive actuator.

11. The display device (3) as claimed in claim 1, further comprising a network interface (25).

12. The display device (3) as claimed in claim 1, further comprising a delay element with which a movement of the at least one display element (4) from the display position back into the initial position is delayed.

13. A liquid dispenser (1) comprising a delivery device (2) for delivering liquid, and the display device (3) as claimed in claim 1.

14. The liquid dispenser (1) as claimed in claim 13, wherein the delivery device (2) is connected to the interface (6) of the drive actuator.

15. The liquid dispenser (1) as claimed in claim 13, wherein the delivery liquid comprises at least one of a disinfectant or a cleaning agent.

16. The display device (3) as claimed in claim 1, further comprising at least one of an optical signal transducer (12) or an acoustic signal transducer (13).

17. The display device (3) as claimed in claim 1, further comprising a limiting stop (34) which prevents further movement of the display element (4) beyond the display position.

18. The display device (3) as claimed in claim 1, wherein the at least one display element (4) of the display device (3) is a sign support or a figure support.

19. The display device (3) as claimed in claim 1, wherein after actuation of the delivery device, the display element (4) returns from the visible display position to the initial position.

\* \* \* \* \*